United States Patent
Tryggvason et al.

(10) Patent No.: US 9,719,066 B2
(45) Date of Patent: *Aug. 1, 2017

(54) STEM CELL BANK

(71) Applicant: BioLamina AB, Sundbyberg (SE)

(72) Inventors: Karl Tryggvason, Djursholm (SE); Kristian Tryggvason, Sundbyberg (SE); Outi Hovatta, Solna (SE)

(73) Assignee: BIOLAMINA AB, Sundyberg (SE)

(*) Notice: Subject to any disclaimer, the term of this patent is extended or adjusted under 35 U.S.C. 154(b) by 140 days.

This patent is subject to a terminal disclaimer.

(21) Appl. No.: 14/419,517

(22) PCT Filed: Sep. 6, 2013

(86) PCT No.: PCT/IB2013/002548
§ 371 (c)(1),
(2) Date: Feb. 4, 2015

(87) PCT Pub. No.: WO2014/037807
PCT Pub. Date: Mar. 13, 2014

(65) Prior Publication Data
US 2015/0191694 A1 Jul. 9, 2015

Related U.S. Application Data

(60) Provisional application No. 61/716,104, filed on Oct. 19, 2012, provisional application No. 61/698,238, filed on Sep. 7, 2012.

(51) Int. Cl.
*C12N 5/00* (2006.01)
*C12N 5/071* (2010.01)
*C12N 5/073* (2010.01)
*C12N 5/0735* (2010.01)

(52) U.S. Cl.
CPC ......... *C12N 5/0602* (2013.01); *C12N 5/0603* (2013.01); *C12N 5/0606* (2013.01); *C12N 2500/30* (2013.01); *C12N 2500/98* (2013.01); *C12N 2533/52* (2013.01)

(58) Field of Classification Search
CPC ... C12N 5/0602; C12N 5/0603; C12N 5/0606
See application file for complete search history.

(56) References Cited

U.S. PATENT DOCUMENTS 7,811,819 B2 * 10/2010 Ware .................. A01N 1/02
435/325
2004/0091936 A1 * 5/2004 West .................. C12N 5/0606
435/7.1
2008/0057041 A1 3/2008 Chung et al.
2009/0075322 A1 * 3/2009 Short .................. C12N 5/0068
435/29
2012/0156254 A1 6/2012 Tryggvason et al.
2014/0315306 A1 * 10/2014 Tryggvason ......... C07K 14/705
435/377

FOREIGN PATENT DOCUMENTS

WO WO 2011/110886 A1 9/2011
WO WO 2013/041961 A1 3/2013

OTHER PUBLICATIONS

Nagaoka et al. BMC Developmental Biology 10:60, pp. 1-12, 2010.*
Rodin et al., "Long-term self-renewal of human pluripotent stem cells on human recombinant laminin-511", Nature Biotechnology, Nature Publishing Group, New York, NY, US, vol. 28, No. 6, Jun. 1, 2010, pp. 611-615.
Chung et al., "Human embryonic stem cell lines generated without embryo destruction", Cell Stem Cell, Elsevier, Cell Press, Amsterdam, NL, vol. 2, No. 2, Feb. 7, 2008, pp. 113-117.
Nie et al., "Scalable culture and cryopreservation of human embryonic stem cells on microcarriers", Biotechnology Progress, American Institute of Chemical Engineers, US, vol. 25, No. 1, Jan. 1, 2009, pp. 20-31.
Domogatskaya et al., "Laminin-511 but not -332, -111, or -411 enables mouse embryonic stem cell self-renewal in vitro", Stem Cells, Alphamed Press, Inc., US, vol. 26, No. 11, Nov. 1, 2008, pp. 2800-2809.
Taylor et al., "Immunological considerations for embryonic and induced pluripotent stem call banking", Development, vol. 120, No. 6, Jul. 4, 2011, pp. 1651-2322.
Rodin et al., "Clonal culturing of human embryonic stem cells on laminin-521/E-cadherin matrix in defined and xeno-free environment", Nature Communications, vol. 5, Jan. 27, 2014.

* cited by examiner

*Primary Examiner* — Marcia S Noble
(74) *Attorney, Agent, or Firm* — Richard M. Klein; Fay Sharpe LLP (57) ABSTRACT

The present disclosure is related to methods for forming a stem cell bank. The methods include obtaining a first stem cell from a multi-cell fertilized embryo, expanding the first stem cell into two or more descendant stem cells, and storing at least one of the descendant stem cells to form the stem cell bank. Also disclosed is a kit that can be used for making the stem cell bank during in vitro fertilization. If desired, the HLA serotype of the stem cells can be determined prior to storage.

15 Claims, 3 Drawing Sheets

STEM CELL BANK

CROSS-REFERENCE TO RELATED APPLICATIONS

This application claims priority to U.S. Provisional Application No. 61/698,238, filed Sep. 7, 2012, and to U.S. Provisional Application No. 61/716,104, filed Oct. 19, 2012. The disclosures of these applications are hereby fully incorporated by reference herein.

BACKGROUND

Human stem cells, which include human embryonic stem cells (hESCs) as well as induced pluripotent stem cells (iPSCs), may be useful for cellular therapies for regenerative medicine and treating a variety of diseases, such as spinal cord and cardiac injuries. A stem cell is an undifferentiated cell from which specialized cells are subsequently derived. Embryonic stem cells possess extensive self-renewal capacity and pluripotency with the potential to differentiate into cells of all three germ layers.

A stem cell bank, which is a collection of stem cells, may be useful for research and for future use in regenerative medicine. Ideally, the stem cells collected for the stem cell bank can retain their pluripotent state for a long period of time. In addition, the stem cells should not be contaminated with xenogeneic reagents.

BRIEF DESCRIPTION

Disclosed herein are methods for forming a stem cell bank from a single blastomere/stem cell of an embryo without destroying the embryo. This would permit stem cell banks to be formed from embryos that are fertilized in vitro or in vivo and permit normal development of the embryo. The single blastomere/stem cell is expanded into two or more descendant stem cells. The HLA serotype of the single stem cell or the descendant stem cells can then be determined, if desired. Additionally disclosed are kits for forming such stem cell banks and a HLA serotype stem cell bank.

Disclosed herein are methods for forming a stem cell bank, comprising: obtaining a first stem cell from a multi-cell fertilized embryo; expanding the first stem cell into two or more descendant stem cells; and storing at least one of the descendant stem cells to form the stem cell bank.

The first stem cell may be expanded by placing the first stem cell on a cell culture substrate comprising a laminin and a cadherin, wherein the laminin is an intact protein or a protein fragment. The laminin can be laminin-521 or laminin-511, or any effective recombinant laminin. The cadherin can be e-cadherin. The weight ratio of the laminin to the cadherin can be from about 5:1 to about 15:1, or from about 5:1 to about 10:1.

In particular embodiments, the laminin is laminin-521 and the cadherin is e-cadherin. Sometimes, cell culture substrate consists of the laminin and the cadherin.

The cell culture substrate generally does not contain any differentiation inhibitors, feeder cells, differentiation inductors, or apoptosis inhibitors.

A cell culture medium may also be applied to the first stem cell. The cell culture medium may have an albumin concentration of at least 0.3 mM.

The method may further comprise replating the descendant stem cells on a new cell culture substrate comprising a laminin, wherein the laminin is an intact protein or a protein fragment. The new cell culture substrate does not need to comprise a cadherin. The laminin of the new cell culture substrate may be laminin-521 or laminin-511.

The at least one descendant stem cell can be stored by freezing.

The multi-cell fertilized embryo may have from 8 to 32 total cells. The first stem cell may be obtained from the multi-cell fertilized embryo by splitting the cells of the fertilized embryo. The splitting can be performed by exposing the cells of the fertilized embryo to EDTA or to lytic enzymes.

Also described in various embodiments is a kit for creating a stem cell bank, comprising: a cell culture substrate; a cell culture medium; a cell splitting solution; and a freezing medium. The cell splitting solution may contain EDTA or lytic enzymes. The freezing medium may be liquid nitrogen.

Further disclosed herein are methods for forming a stem cell bank, comprising: obtaining a first stem cell from a multi-cell fertilized embryo; expanding the first stem cell into two or more descendant stem cells; determining the human leukocyte antigen (HLA) serotype of the first stem cell or the two or more descendant stem cells; and storing at least one of the descendant stem cells to form the stem cell bank.

The first stem cell may be expanded by placing the first stem cell on a cell culture substrate comprising a laminin and a cadherin, wherein the laminin is an intact protein or a protein fragment. The laminin can be laminin-521 or laminin-511, or any effective recombinant laminin. The cadherin can be e-cadherin. The weight ratio of the laminin to the cadherin can be from about 5:1 to about 15:1, or from about 5:1 to about 10:1.

In particular embodiments, the laminin is laminin-521 and the cadherin is e-cadherin. Sometimes, cell culture substrate consists of the laminin and the cadherin.

The cell culture substrate generally does not contain any differentiation inhibitors, feeder cells, differentiation inductors, or apoptosis inhibitors.

A cell culture medium may also be applied to the first stem cell. The cell culture medium may have an albumin concentration of at least 0.3 mM.

The method may further comprise replating the descendant stem cells on a new cell culture substrate comprising a laminin, wherein the laminin is an intact protein or a protein fragment. The new cell culture substrate does not need to comprise a cadherin. The laminin of the new cell culture substrate may be laminin-521 or laminin-511.

The at least one descendant stem cell can be stored by freezing.

The multi-cell fertilized embryo may have from 8 to 32 total cells. The first stem cell may be obtained from the multi-cell fertilized embryo by splitting the cells of the fertilized embryo. The splitting can be performed by exposing the cells of the fertilized embryo to EDTA or to lytic enzymes.

Also described in various embodiments is a kit for creating a stem cell bank, comprising: a cell culture substrate; a cell culture medium; a cell splitting solution; a HLA serotype analyzer; and a freezing medium. The cell splitting solution may contain EDTA or lytic enzymes. The freezing medium may be liquid nitrogen.

Additionally described in various embodiments is a HLA typed stem cell bank comprising a cryopreservation medium; a first cryotube including a first derived stem cell line representative of a first HLA serotype; and an infrastructure housing the cryopreservation medium and the first cryotube.

These and other non-limiting characteristics of the disclosure are more particularly disclosed below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

A more complete understanding of the compositions and methods disclosed herein can be obtained by reference to the accompanying drawings. These figures are merely schematic representations based on convenience and the ease of demonstrating the present disclosure, and are, therefore, not intended to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

All publications, patents, and patent applications discussed herein are hereby incorporated by reference in their entirety.

As used herein, the term "self-renewal" refers to the ability of the stem cell to go through numerous cycles of cell division and remain undifferentiated (i.e. pluripotent). Pluripotency itself refers to the ability of the stem cell to differentiate into any cell type. The term "proliferation" refers to the ability of the stem cell to divide. Survival refers to the ability of the stem cell to live, whether differentiated or undifferentiated, and does not require the stem cell to maintain its ability to divide or to differentiate.

Figure 1:
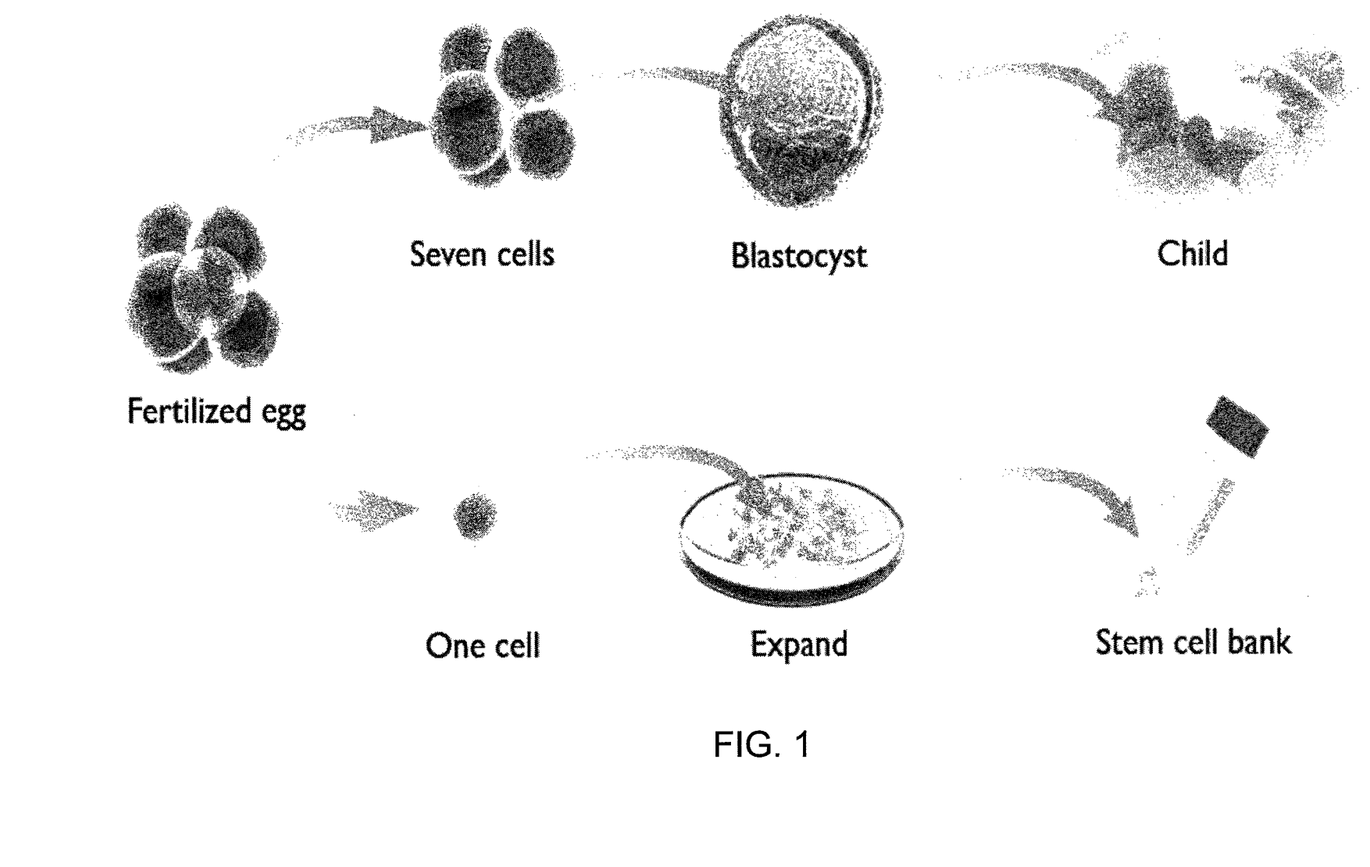
FIG. 1 is a diagram of the overall methods of the present disclosure

The present disclosure relates to methods of forming stem cell banks by obtaining a single stem cell from a multi-cell fertilized embryo. The stem cell can be expanded and then stored to form the stem cell bank. It is contemplated that these methods can be particularly used in conjunction with in vitro fertilization (IVF). An overview of the process is illustrated in FIG. 1. In an initial step starting at the left, a fertilized egg (i.e. zygote) is shown. The fertilized egg undergoes cleavage, increasing from one cell to eight cells. Each cell of the eight-cell embryo can be referred to as a blastomere or as an embryonic stem cell, and these terms are used interchangeably herein. Each of these blastomeres/stem cells is totipotent or pluripotent. One stem cell is removed from the eight-cell embryo. The single stem cell is then expanded to form two or more descendant stem cells. These descendant stem cells are then stored to form the stem cell bank. The remaining seven cells of the embryo can continue on their natural progression, forming a blastocyst and eventually a child. It is noted that the embryo does not need to be destroyed to obtain the single stem cell.

In additional embodiments, the human leukocyte antigen (HLA) serotype of the first stem cell or the two or more descendant stem cells is determined. HLAs are proteins located on the surface of white blood cells and other tissues in the human body. HLAs primarily act as immune system markers. HLAs are used to help the body recognize which cells are natural to the body (i.e. "self") and which cells are foreign (i.e. "non-self"). In the case of stem cell transplantation, a close HLA serotype match between the donor stem cells and the recipient human tissue can reduce the risk of a bodily immune response after implantation or donation. In this regard, the HLA system includes several haplotypes, such as HLA-A, HLA-B, and HLA-DR. Each haplotype can have one of several different alleles, such as HLA-A1. The term "serotype" is used here to refer to the stem cell having a given combination of alleles for each haplotype. For example, a stem cell expressing HLA-A1, HLA-B1, and HLA-DR1 has a different serotype from a stem cell expressing HLA-A1, HLA-B1, and HLA-DR2.

Repeated infusion of recipient human tissue with donor cells having foreign HLA antigens often results in immunization, i.e. an immune system response to the foreign cells. However, certain forms of transplantation appear to circumvent some of the immune surveillance systems found in humans, resulting in acceptance of the HLA-mismatched donor cells. For example, this includes transplantation with cord-blood derived hematopoietic stem cells and mesenchymal stem cells. Because an HLA-identical donor, whether related to the recipient or not, can be found for only approximately 20-40% of patients in need of stem cell transplantation, non-matching HLA serotype stem cell donation is increasingly used. Many techniques may be implemented to control for immune reactivity after non-matching HLA serotype stem cell donation, including administration of a immunosuppressive drug, T-cell depletion of a donor graft containing donor stem cells, or use of a suicide gene to specifically attack alloreactive cells on the recipient human tissue.

In order to minimize the risk of rejection of transplanted stem cells by recipient human tissues (also known as immunogenicity), the stem cell bank may include stem cells which are homozygous for a common HLA haplotype. A haplotype is a combination of alleles (DNA sequences) that are transmitted together. Homozygous means that only one HLA haplotype is expressed by the stem cell, or in other words that the haplotype on both chromosomes is the same. The major HLA haplotypes are HLA-A, HLA-B, and HLA-DR. There are many different specific HLA haplotypes which can be expressed at each locus. Based on the frequency of common HLA haplotypes in, e.g., the Caucasian population, at least one thousand potential embryo donors may need to be HLA typed for HLA-A, HLA-B, and HLA-DRB1 to establish a stem cell bank with homozygous HLA haplotypes.

The utility of the stem cell bank may be enhanced by storing stem cell lines representing most human leukocyte antigen (HLA) serotypes. A stem cell bank including HLA typed stem cells may prove useful for overcoming immunogenicity problems which occur during transplantation of stem cells into different human tissues.

Such a stem cell bank including derived hESC cell lines homozygous for HLA haplotypes does not currently exist. Generation of the stem cell bank would aid those individuals who have undergone HLA-mismatched transplants and therefore require constant immunosuppressive therapy. The stem cell bank would also reduce the chance of infection after implantation. For tissues that may be infected by virus, HLA class I identity between recipient tissue and donor stem cells is required for T-cells to kill virus infected transplanted cells. The stem cell bank may be used for research and clinical purposes, and would be unique in the world.

A worthwhile HLA match for a reasonable percentage of the United Kingdom population could be provided by approximately 150 random donors, and 100 selected blood group O donors would provide an ABO blood type compatible and full HLA-A, HLA-B, and HLA-DR match for only a minority (less than 20%) of potential recipients and a beneficial match (defined as a single HLA-A or HLA-B mismatch or better) for around 38 percent of recipients. Good HLA matching has been observed in a higher proportion of white Europeans than those of Asian and African ethnicity. Extending the number of donors beyond 150 would confer only marginal additional benefits with respect to HLA matching.

The stem cell bank including derived stem cell lines homozygous for HLA haplotypes would provide extraordinary HLA matching with a relatively small sample size. For example, a panel of ten highly selected donors homozygous for conserved HLA haplotypes would be expected to provide a complete HLA-A, HLA-B, HLA-DR match for around 38 percent of potential recipients and a beneficial match for 67 percent of recipients. This is in contrast to the 150 random donors and 100 selected donors mentioned above, which include substantially larger donor groups with substantially worse HLA matching percentages.

In an alternative embodiment, immunogenicity may be further reduced by selecting "permissive" HLA-mismatches. The stem cell bank may include not only common and/or specific HLA serotypes, but also those which are permissive mismatches for targeted HLA serotypes. A permissive HLA mismatch may be determined by an algorithm which defines permissive and non-permissive mismatches based on the cross reactivity of T-cells between donor stem cell graft and recipient human tissue. A permissive mismatch in HLA serotypes would be indicated by a minimal cross reactivity of T-cells.

Generally, the blastomere/stem cell can be obtained before compaction of the morula, after compaction of the morula, before formation of the blastocoel, or during the blastocyst stage. The blastomere/stem cell is present in the inner cell mass of the blastocyst.

Figure 2:
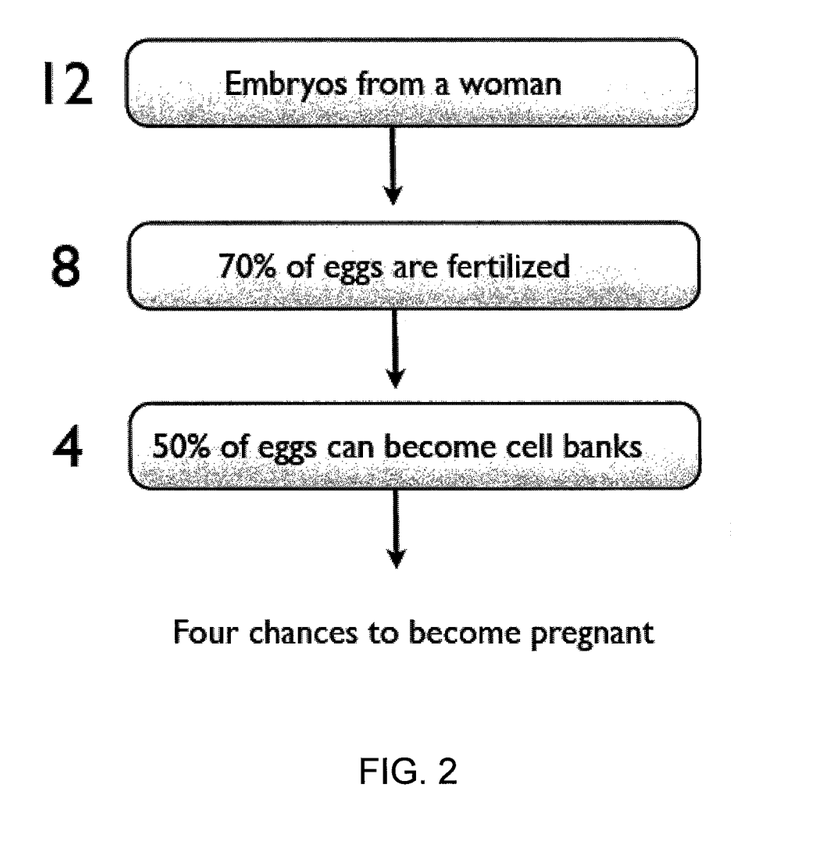
FIG. 2 is a diagram showing the combination of the overall methods with in vitro fertilization.

FIG. 2 is a diagram illustrating the suitability of combining the present methods of forming a stem cell bank with in vitro fertilization (IVF), showing that no major changes in current IVF protocols are needed. During IVF, 12 eggs are typically harvested from a woman. Of the twelve eggs, approximately 70% (or eight out of twelve) will become fertilized after incubation of sperm and egg together. Of the eight fertilized eggs, four could be used in subsequent selection, expansion, and storage to form a stem cell bank. Four fertilized eggs can still be used for the typical IVF process, leaving four chances for pregnancy.

The single stem cell can be obtained from the multi-cell fertilized embryo by splitting the single stem cell from the rest of the embryo. Again, it should be noted that at this early stage, each cell of the embryo can be considered to be a stem cell. The splitting can be done using methods known in the art. For example, ethylenediamine tetracetic acid (EDTA) can be used to split off the single stem cell. Another commercially available product is Accutase®, which is a collection of lytic (i.e. cutting) enzymes.

During expansion, stem cells typically require two things to proliferate: (1) a substrate or coating that provides a structural support for the stem cell; and (2) a cell culture medium to provide nutrition to the stem cell. The substrate or coating (1) is generally placed on, for example, a petri dish or some other container. It is particularly contemplated that the single stem cell which is harvested from the eight-cell embryo is expanded by placing the stem cell on a cell culture substrate comprising a laminin and a cadherin.

Laminins are a family of heterotrimeric glycoproteins that reside primarily in the basal lamina. They function via binding interactions with neighboring cell receptors on the one side, and by binding to other laminin molecules or other matrix proteins such as collagens, nidogens or proteoglycans. The laminin molecules are also important signaling molecules that can strongly influence cellular behavior and function. Laminins are important in both maintaining cell/tissue phenotype, as well as in promoting cell growth and differentiation in tissue repair and development.

Laminins are large, multi-domain proteins, with a common structural organization. The laminin molecule integrates various matrix and cell interactive functions into one molecule.

Figure 3:
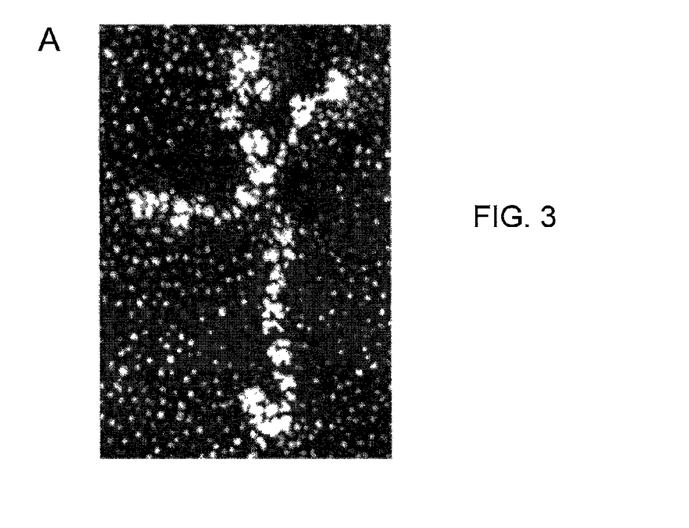
FIG. 3 is a rotary shadowing electron microscopy picture of a recombinant laminin molecule.
Figure 4:
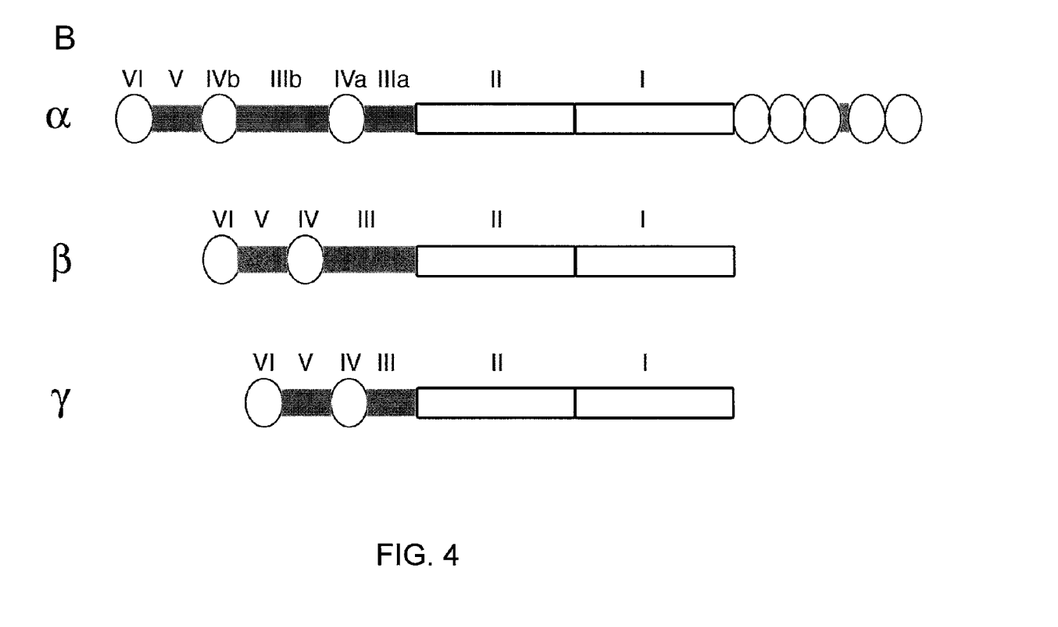
FIG. 4 shows the structural motifs of laminin α, β, and γ chains. The N-terminal, internal, and C-terminal globular domains are depicted as white ovals. The coiled-coil forming domains (I and II) are shown as white rectangles. The rod-like structures (domains V, IIIb, and IIIa) are depicted as grey rectangles.

A laminin protein molecule comprises one α-chain subunit, one β-chain subunit, and one γ-chain subunit, all joined together in a trimer through a coiled-coil domain. FIG. 3 depicts the resulting structure of the laminin molecule. The twelve known laminin subunit chains can form at least 15 trimeric laminin types in native tissues. Within the trimeric laminin structures are identifiable domains that possess binding activity towards other laminin and basal lamina molecules, and membrane-bound receptors. FIG. 4 shows the three laminin chain subunits separately. For example, domains VI, IVb, and IVa form globular structures, and domains V, IIIb, and IIIa (which contain cysteine-rich EGF-like elements) form rod-like structures. Domains I and II of the three chains participate in the formation of a triple-stranded coiled-coil structure (the long arm).

There exist five different alpha chains, three beta chains and three gamma chains that in human tissues have been found in at least fifteen different combinations. These molecules are termed laminin-1 to laminin-15 based on their historical discovery, but an alternative nomenclature describes the isoforms based on their chain composition, e.g. laminin-111 (laminin-1) that contains alpha-1, beta-1 and gamma-1 chains. Four structurally defined family groups of laminins have been identified. The first group of five identified laminin molecules all share the β1 and γ1 chains, and vary by their α-chain composition (α1 to α5 chain). The second group of five identified laminin molecules, including laminin-521, all share the β2 and γ1 chain, and again vary by their α-chain composition. The third group of identified laminin molecules has one identified member, laminin-332, with a chain composition of α3β3γ2. The fourth group of identified laminin molecules has one identified member, laminin-213, with the newly identified γ3 chain (α2β1γ3).

Generally, the cell culture substrate may contain any effective laminin, wherein the effectiveness is determined by whether stem cells can proliferate upon the substrate. It is specifically contemplated that the substrate contains only one particular laminin, though other ingredients are also present in the substrate. In specific embodiments, the laminin is laminin-521 (LN-521) or laminin-511 (LN-511).

The term "laminin-521" refers to the protein formed by joining α5, β2 and γ1 chains together. The term "laminin- 511" refers to the protein formed by joining α5, β1 and γ1 chains together. These terms should be construed as encompassing both the recombinant laminin and heterotrimeric laminin from naturally occurring sources. The term "recombinant" indicates that the protein is artificially produced in cells that do not normally express such proteins.

The laminin can be an intact protein or a protein fragment. The term "intact" refers to the protein being composed of all of the domains of the α-chain, β-chain, and γ-chain, with the three chains being joined together to form the heterotrimeric structure. The protein is not broken down into separate chains, fragments, or functional domains. The term "chain" refers to the entirety of the alpha, beta, or gamma chain of the laminin protein. The term "fragment" refers to any protein fragment which contains one, two, or three functional domains that possesses binding activity to another molecule or receptor. However, a chain should not be considered a fragment because each chain possesses more than three such domains. Similarly, an intact laminin protein should not be considered a fragment. Examples of functional domains include Domains I, II, III, IV, V, VI, and the G domain.

The average contact area and spreading homogeneity is much larger for cells cultured on laminin-511 compared to other available substrata. Human ES cells grown on laminin-511 over 3 months maintain pluripotency and can generate teratomas after engraftment into SCID mice. Laminin-511 also supports the self-renewal of mouse ES cells for over 5 months without the presence of LIF or feeder cells, when other known matrices are unable to do so for longer than a couple of weeks.

The cell culture substrate also comprises a cadherin. Cadherins are a class of type-1 transmembrane proteins that play important roles in cell adhesion, ensuring that cells within tissues are bound together. They are dependent on calcium ($Ca^{2+}$) ions to function. Cadherins are also known as desmogleins and desmocollins. Structurally, cadherins contain extracellular $Ca^{2+}$-binding domains. In particular embodiments, the cadherin used in the cell culture substrate is epithelial cadherin or e-cadherin.

The weight ratio of the laminin to the cadherin may be from about 5:1 to about 15:1, or from about 5:1 to about 10:1. In particular embodiments, the cell culture substrate consists of the laminin and the cadherin. In other specific embodiments, the laminin is laminin-521 and the cadherin is e-cadherin.

The cell culture substrate is used in combination with a cell culture medium. The cell culture medium of the present disclosure is particularly suitable for being used with a substrate that contains laminin-521 and/or laminin-511. These laminins activate α6β1 integrins, which in turn leads to activation of the PI3K/Akt pathway. This increases the pluripotency, self-renewal, and/or proliferation of the stem cells. It is contemplated that the substrate may consist of laminin-521 or laminin-511, either intact, as separate chains, or as fragments thereof. Recombinant laminin-521 and recombinant laminin-511 are commercially available. Many different molecules can activate the PI3K/Akt pathway, though with different efficiencies. For example, TGF beta 1 and bFGF activate this pathway. The use of laminin-521 and/or laminin-511 allows the quantity of such molecules to be reduced in the cell culture medium. Laminin-521 conveys the highest dose of signal via α6β1 integrin, activating the PI3K/Akt pathway. The use of laminin-521 allows for single-cell suspension passaging without the addition of cell-detrimental rho-kinase (ROCK) inhibitor to increase cell survival after single-cell enzymatic dissociation. Previously, single-cell enzymatic passage of human ES cells without using artificial apoptosis inhibitors was impossible. The simplicity of the passaging procedure means the experimental variance is reduced and allows the process to be automated for high-throughput cell culture and results without the extensive training and costs of cell culture staff. In addition, human ES and iPS cells plated on laminin-521 or laminin-511 grow as a monolayer, which makes the culture homogeneous since cells are equally exposed to the matrix and the cell culture medium. Such human ES cell cultures, grown in a chemically defined, xeno-free environment on laminin-521, passaged as single cells in the absence of ROCK inhibitor expand continuously for months at an even better growth rate compared to cells grown on Matrigel passaged as clumps. These pluripotent long-term expanded cells homogeneously express Oct4 and remain karyotypically normal. Thus, one can obtain human ES and iPS cells with sustained survival and proliferation capacity.

Typically, cell culture media include a large number and a large amount of various growth factors and cytokines to inhibit differentiation and improve proliferation. One advantage of the cell culture medium of the present disclosure is that it does not contain as many growth factors or cytokines, or such high amounts.

Very generally, the cell culture medium of the present disclosure requires lower amounts of basic fibroblast growth factor (bFGF) than typically used. It is contemplated that the cell culture medium may comprise from greater than zero to 3.9 nanograms per milliliter (ng/mL) of bFGF. The bFGF is human bFGF so that the cell culture medium is totally human and defined. In some more specific embodiments, the cell culture medium may comprise 3.5 or lower ng/mL of bFGF. In other embodiments, the cell culture medium may comprise from 0.5 to 3.5 ng/mL of bFGF. In some embodiments, the cell culture medium may have zero bFGF, i.e. no bFGF is present.

Generally, the cell culture medium includes a liquid phase in which at least one inorganic salt, at least one trace mineral, at least one energy substrate, at least one lipid, at least one amino acid, at least one vitamin, and at least one growth factor (besides bFGF) are dissolved. Table 1 below includes a list of various such ingredients which may be present in the cell culture medium of the present disclosure, and the minimum and maximum concentrations if the ingredient is present. The values are presented in scientific notation. For example, "4.1E-01" should be interpreted as $4.1 \times 10^{-01}$.

TABLE 1

| Ingredient | molar mass (g/mol) | Min. Conc. (mM) | Max. Conc. (mM) | Min. Conc. (ng/mL) | Max. Conc. (ng/mL) |
|---|---|---|---|---|---|
| INORGANIC SALTS | | | | | |
| Calcium chloride (Anhydrous) | 110.98 | 4.1E−01 | 1.6E+00 | 4.6E+04 | 1.8E+05 |

TABLE 1-continued

| Ingredient | molar mass (g/mol) | Min. Conc. (mM) | Max. Conc. (mM) | Min. Conc. (ng/mL) | Max. Conc. (ng/mL) |
|---|---|---|---|---|---|
| HEPES | 238.3 | 5.9E+00 | 1.8E+01 | 1.4E+06 | 4.2E+06 |
| Lithium Chloride (LiCl) | 42.39 | 4.9E−01 | 1.5E+00 | 2.1E+04 | 6.2E+04 |
| Magnesium chloride (Anhydrous) | 95.21 | 1.2E−01 | 3.6E−01 | 1.1E+04 | 3.4E+04 |
| Magnesium Sulfate ($MgSO_4$) | 120.37 | 1.6E−01 | 4.8E−01 | 1.9E+04 | 5.8E+04 |
| Potassium chloride (KCl) | 74.55 | 1.6E+00 | 4.9E+00 | 1.2E+05 | 3.6E+05 |
| Sodium bicarbonate ($NaHCO_3$) | 84.01 | 9.0E+00 | 4.4E+01 | 7.6E+05 | 3.7E+06 |
| Sodium chloride (NaCl) | 58.44 | 4.7E+01 | 1.4E+02 | 2.8E+06 | 8.3E+06 |
| Sodium phosphate, dibasic (Anhydrous) | 141.96 | 2.0E−01 | 5.9E−01 | 2.8E+04 | 8.3E+04 |
| Sodium phosphate, monobasic monohydrate ($NaH_2PO_4$—$H_2O$) | 137.99 | 1.8E−01 | 5.3E−01 | 2.4E+04 | 7.3E+04 |
| TRACE MINERALS | | | | | |
| Ferric Nitrate ($Fe(NO_3)_3$—$9H_2O$) | 404 | 4.9E−05 | 1.9E−04 | 2.0E+01 | 7.5E+01 |
| Ferrous sulfate heptahydrate ($FeSO_4$—$7H_2O$) | 278.01 | 5.9E−04 | 1.8E−03 | 1.6E+02 | 4.9E+02 |
| Copper(II) sulfate pentahydrate ($CuSO_4$—$5H_2O$) | 249.69 | 2.0E−06 | 8.0E−06 | 5.1E−01 | 2.0E+00 |
| Zinc sulfate heptahydrate ($ZnSO_4$—$7H_2O$) | 287.56 | 5.9E−04 | 1.8E−03 | 1.7E+02 | 5.1E+02 |
| Ammonium Metavanadate $NH_4VO_3$ | 116.98 | 5.5E−06 | 1.6E−05 | 6.4E−01 | 1.9E+00 |
| Manganese Sulfate monohydrate ($MnSO_4$—$H_2O$) | 169.02 | 9.9E−07 | 3.0E−06 | 1.7E−01 | 5.0E−01 |
| $NiSO_4$—$6H_2O$ | 262.85 | 4.9E−07 | 1.5E−06 | 1.3E−01 | 3.8E−01 |
| Selenium | 78.96 | 8.9E−05 | 2.7E−04 | 7.0E+00 | 2.1E+01 |
| Sodium Meta Silicate $Na_2SiO_3$—$9H_2O$ | 284.2 | 4.8E−04 | 1.4E−03 | 1.4E+02 | 4.1E+02 |
| $SnCl_2$ | 189.62 | 6.2E−07 | 1.9E−06 | 1.2E−01 | 3.5E−01 |
| Molybdic Acid, Ammonium salt | 1235.86 | 9.9E−07 | 3.0E−06 | 1.2E+00 | 3.7E+00 |
| $CdCl_2$ | 183.32 | 6.1E−06 | 1.8E−05 | 1.1E+00 | 3.4E+00 |
| $CrCl_3$ | 158.36 | 9.9E−07 | 3.0E−06 | 1.6E−01 | 4.7E−01 |
| $AgNO_3$ | 169.87 | 4.9E−07 | 1.5E−06 | 8.3E−02 | 2.5E−01 |
| $AlCl_3$—$6H_2O$ | 241.43 | 2.4E−06 | 7.3E−06 | 5.9E−01 | 1.8E+00 |
| Barium Acetate ($Ba(C_2H_3O_2)_2$) | 255.42 | 4.9E−06 | 1.5E−05 | 1.3E+00 | 3.8E+00 |
| $CoCl_2$—$6H_2O$ | 237.93 | 4.9E−06 | 1.5E−05 | 1.2E+00 | 3.5E+00 |
| $GeO_2$ | 104.64 | 2.5E−06 | 7.5E−06 | 2.6E−01 | 7.8E−01 |
| KBr | 119 | 4.9E−07 | 1.5E−06 | 5.9E−02 | 1.8E−01 |
| KI | 166 | 5.0E−07 | 1.5E−06 | 8.3E−02 | 2.5E−01 |
| NaF | 41.99 | 4.9E−05 | 1.5E−04 | 2.1E+00 | 6.2E+00 |
| RbCl | 120.92 | 4.9E−06 | 1.5E−05 | 5.9E−01 | 1.8E+00 |
| $ZrOCl_2$—$8H_2O$ | 178.13 | 4.9E−06 | 1.5E−05 | 8.7E−01 | 2.6E+00 |
| ENERGY SUBSTRATES | | | | | |
| D-Glucose | 180.16 | 6.9E+00 | 2.1E+01 | 1.2E+06 | 3.7E+06 |
| Sodium Pyruvate | 110.04 | 2.0E−01 | 5.9E−01 | 2.2E+04 | 6.5E+04 |
| LIPIDS | | | | | |
| Linoleic Acid | 280.45 | 9.4E−05 | 2.8E−04 | 2.6E+01 | 7.9E+01 |
| Lipoic Acid | 206.33 | 2.0E−04 | 7.8E−04 | 4.1E+01 | 1.6E+02 |
| Arachidonic Acid | 304.47 | 6.5E−06 | 1.9E−05 | 2.0E+00 | 5.9E+00 |
| Cholesterol | 386.65 | 5.6E−04 | 1.7E−03 | 2.2E+02 | 6.5E+02 |
| DL-alpha tocopherol-acetate | 472.74 | 1.5E−04 | 4.4E−04 | 6.9E+01 | 2.1E+02 |
| Linolenic Acid | 278.43 | 3.5E−05 | 1.0E−04 | 9.7E+00 | 2.9E+01 |
| Myristic Acid | 228.37 | 4.3E−05 | 1.3E−04 | 9.8E+00 | 2.9E+01 |
| Oleic Acid | 282.46 | 3.5E−05 | 1.0E−04 | 9.8E+00 | 2.9E+01 |
| Palmitic Acid | 256.42 | 3.8E−05 | 1.1E−04 | 9.8E+00 | 2.9E+01 |
| Palmitoleic acid | 254.408 | 3.9E−05 | 1.2E−04 | 9.8E+00 | 2.9E+01 |
| Stearic Acid | 284.48 | 3.4E−05 | 1.0E−04 | 9.8E+00 | 2.9E+01 |
| AMINO ACIDS | | | | | |
| L-Alanine | 89.09 | 2.5E−02 | 2.1E−01 | 2.2E+03 | 1.8E+04 |
| L-Arginine hydrochloride | 147.2 | 2.7E−01 | 1.5E+00 | 4.0E+04 | 2.2E+05 |
| L-Asparagine-$H_2O$ | 150.13 | 5.0E−02 | 2.1E−01 | 7.5E+03 | 3.1E+04 |
| L-Aspartic acid | 133.1 | 2.5E−02 | 2.1E−01 | 3.3E+03 | 2.7E+04 |

TABLE 1-continued

| Ingredient | molar mass (g/mol) | Min. Conc. (mM) | Max. Conc. (mM) | Min. Conc. (ng/mL) | Max. Conc. (ng/mL) |
|---|---|---|---|---|---|
| L-Cysteine-HCl—H$_2$O | 175.63 | 3.9E−02 | 1.2E−01 | 6.9E+03 | 2.1E+04 |
| L-Cystine dihydrochloride | 313.22 | 3.9E−02 | 1.2E−01 | 1.2E+04 | 3.7E+04 |
| L-Glutamic acid | 147.13 | 2.5E−02 | 2.1E−01 | 3.7E+03 | 3.0E+04 |
| L-Glutamine | 146.15 | 1.5E+00 | 4.4E+00 | 2.1E+05 | 6.4E+05 |
| Glycine | 75.07 | 1.5E−01 | 4.4E−01 | 1.1E+04 | 3.3E+04 |
| L-Histidine monohydrochloride monohydrate | 209.63 | 5.9E−02 | 1.8E−01 | 1.2E+04 | 3.7E+04 |
| L-Isoleucine | 131.17 | 1.6E−01 | 4.9E−01 | 2.1E+04 | 6.4E+04 |
| L-Leucine | 131.17 | 1.8E−01 | 5.3E−01 | 2.3E+04 | 7.0E+04 |
| L-Lysine hydrochloride | 182.65 | 2.0E−01 | 5.9E−01 | 3.6E+04 | 1.1E+05 |
| L-Methionine | 149.21 | 4.5E−02 | 1.4E−01 | 6.8E+03 | 2.0E+04 |
| L-Phenylalanine | 165.19 | 8.5E−02 | 2.5E−01 | 1.4E+04 | 4.2E+04 |
| L-Proline | 115.13 | 1.1E−01 | 3.2E−01 | 1.2E+04 | 3.7E+04 |
| L-Serine | 105.09 | 1.5E−01 | 4.4E−01 | 1.5E+04 | 4.6E+04 |
| L-Threonine | 119.12 | 1.8E−01 | 5.3E−01 | 2.1E+04 | 6.3E+04 |
| L-Tryptophan | 204.23 | 1.7E−02 | 5.2E−02 | 3.5E+03 | 1.1E+04 |
| L-Tyrosine disodium salt hydrate | 225.15 | 8.4E−02 | 3.7E−01 | 1.9E+04 | 8.4E+04 |
| L-Valine | 117.15 | 1.8E−01 | 5.3E−01 | 2.1E+04 | 6.2E+04 |
| VITAMINS | | | | | |
| Ascorbic acid | 176.12 | 1.3E−01 | 3.8E−01 | 2.2E+04 | 6.7E+04 |
| Biotin | 244.31 | 5.6E−06 | 1.7E−05 | 1.4E+00 | 4.1E+00 |
| B$_{12}$ | 1355.37 | 2.0E−04 | 5.9E−04 | 2.7E+02 | 8.0E+02 |
| Choline chloride | 139.62 | 2.5E−02 | 7.5E−02 | 3.5E+03 | 1.1E+04 |
| D-Calcium pantothenate | 238.27 | 1.8E−03 | 1.4E−02 | 4.4E+02 | 3.4E+03 |
| Folic acid | 441.4 | 2.4E−03 | 7.1E−03 | 1.0E+03 | 3.1E+03 |
| i-Inositol | 180.16 | 2.7E−02 | 1.1E−01 | 4.9E+03 | 1.9E+04 |
| Niacinamide | 122.12 | 6.5E−03 | 2.0E−02 | 7.9E+02 | 2.4E+03 |
| Pyridoxine hydrochloride | 205.64 | 3.8E−03 | 1.1E−02 | 7.8E+02 | 2.4E+03 |
| Riboflavin | 376.36 | 2.3E−04 | 6.8E−04 | 8.6E+01 | 2.6E+02 |
| Thiamine hydrochloride | 337.27 | 3.3E−03 | 3.6E−02 | 1.1E+03 | 1.2E+04 |
| GROWTH FACTORS/PROTEINS | | | | | |
| GABA | 103.12 | 0 | 1.5E+00 | 0 | 1.5E+05 |
| Pipecolic Acid | 129 | 0 | 1.5E−03 | 0 | 1.9E+02 |
| bFGF | 18000 | 0 | 2.17E−07 | 0 | 3.9E+00 |
| TGF beta 1 | 25000 | 0 | 3.5E−08 | 0 | 8.8E−01 |
| Human Insulin | 5808 | 0 | 5.9E−03 | 0 | 3.4E+04 |
| Human Holo-Transferrin | 78500 | 0 | 2.1E−04 | 0 | 1.6E+04 |
| Human Serum Albumin | 67000 | 0 | 2.9E−01 | 0 | 2.0E+07 |
| Glutathione (reduced) | 307.32 | 0 | 9.6E−03 | 0 | 2.9E+03 |
| OTHER COMPONENTS | | | | | |
| Hypoxanthine Na | 136.11 | 5.9E−03 | 2.6E−02 | 8.0E+02 | 3.6E+03 |
| Phenol red | 354.38 | 8.5E−03 | 2.5E−02 | 3.0E+03 | 9.0E+03 |
| Putrescine-2HCl | 161.07 | 2.0E−04 | 5.9E−04 | 3.2E+01 | 9.5E+01 |
| Thymidine | 242.229 | 5.9E−04 | 1.8E−03 | 1.4E+02 | 4.3E+02 |
| 2-mercaptoethanol | 78.13 | 4.9E−02 | 1.5E−01 | 3.8E+03 | 1.1E+04 |
| Pluronic F-68 | 8400 | 1.2E−02 | 3.5E−02 | 9.8E+04 | 2.9E+05 |
| Tween 80 | 1310 | 1.6E−04 | 4.9E−04 | 2.2E+02 | 6.5E+02 |

The liquid phase of the cell culture medium may be water, serum, or albumin.

Many of the ingredients or components listed above in Table 1 are not necessary, or can be used in lower concentrations.

It is contemplated that the cell culture medium may contain insulin or an insulin substitute. Similarly, the cell culture medium may contain transferrin or a transferrin substitute. However, in more specific embodiments, it is contemplated that the cell culture medium may not be (1) insulin or insulin substitute, or (2) transferrin or transferrin substitute, or any combination of these two components.

It should be noted that other cell culture mediums may contain growth factors such as interleukin-1 beta (IL-1β or catabolin), interleukin-6 (IL6), or pigment epithelium derived factor (PEDF). Such growth factors are not present in the cell culture medium of the present disclosure.

One specific formula for a cell culture medium is provided in Table 2:

TABLE 2

| Ingredient | Amount | Unit |
|---|---|---|
| bFGF | 0.39 | microgram (μg) |
| Albumin | 1.34 | milligram (mg) |
| Insulin | 2 | mg |
| Lithium Chloride | 4.23 | mg |
| GABA | 0.01 | mg |
| TGF beta 1 | 0.06 | μg |
| Pipecolic acid | 0.013 | mg |
| L-glutamine | 2.92 | grams |
| MEM non-essential amino acid solution | 1 | mL |
| DMEM/F12 | 100 | mL |

In this regard, MEM non-essential amino acid solution is typically provided in a 100× concentrate. The MEM of Table 2 is used after dilution back to 1×, and contains the following amino acids in the following concentration listed in Table 3:

TABLE 3

| MEM Amino Acids | Concentration (ng/mL) |
|---|---|
| Glycine | 7.50E+03 |
| L-Alanine | 8.90E+03 |
| L-Asparagine | 1.32E+04 |
| L-Aspartic acid | 1.33E+04 |
| L-Proline | 1.15E+04 |
| L-Serine | 1.05E+04 |

DMEM/F12 contains the following ingredients listed in Table 4:

TABLE 4

| DMEM/F12 Ingredients | Concentration (ng/mL) |
|---|---|
| Glycine | 187.5 |
| L-Alanine | 44.5 |
| L-Arginine hydrochloride | 1475 |
| L-Asparagine-$H_2O$ | 75 |
| L-Aspartic acid | 66.5 |
| L-Cysteine hydrochloride-$H_2O$ | 175.6 |
| L-Cystine 2HCl | 312.9 |
| L-Glutamic Acid | 73.5 |
| L-Glutamine | 3650 |
| L-Histidine hydrochloride-$H_2O$ | 314.8 |
| L-Isoleucine | 544.7 |
| L-Leucine | 590.5 |
| L-Lysine hydrochloride | 912.5 |
| L-Methionine | 172.4 |
| L-Phenylalanine | 354.8 |
| L-Proline | 172.5 |
| L-Serine | 262.5 |
| L-Threonine | 534.5 |
| L-Tryptophan | 90.2 |
| L-Tyrosine disodium salt dihydrate | 557.9 |
| L-Valine | 528.5 |
| Biotin | 0.035 |
| Choline chloride | 89.8 |
| D-Calcium pantothenate | 22.4 |
| Folic Acid | 26.5 |
| Niacinamide | 20.2 |
| Pyridoxine hydrochloride | 20 |
| Riboflavin | 2.19 |
| Thiamine hydrochloride | 21.7 |
| Vitamin $B_{12}$ | 6.8 |
| i-Inositol | 126 |
| Calcium Chloride ($CaCl_2$) (anhyd.) | 1166 |
| Cupric sulfate ($CuSO_4$—$5H_2O$) | 0.013 |
| Ferric Nitrate ($Fe(NO_3)_3$—$9H_2O$) | 0.5 |
| Ferric sulfate ($FeSO_4$—$7H_2O$) | 4.17 |
| Magnesium Chloride (anhydrous) | 286.4 |
| Magnesium Sulfate ($MgSO_4$) (anhyd.) | 488.4 |
| Potassium Chloride (KCl) | 3118 |
| Sodium Bicarbonate ($NaHCO_3$) | 24380 |
| Sodium Chloride (NaCl) | 69955 |
| Sodium Phosphate dibasic ($Na_2HPO_4$) anhydrous | 710.2 |
| Sodium Phosphate monobasic ($NaH_2PO_4$—$H_2O$) | 625 |
| Zinc sulfate ($ZnSO_4$—$7H_2O$) | 4.32 |
| D-Glucose (Dextrose) | 31510 |
| Hypoxanthine Na | 23.9 |
| Linoleic Acid | 0.42 |
| Lipoic Acid | 1.05 |
| Phenol Red | 81 |

TABLE 4-continued

| DMEM/F12 Ingredients | Concentration (ng/mL) |
|---|---|
| Putrescine 2HCl | 0.81 |
| Sodium Pyruvate | 550 |
| Thymidine | 3.65 |

In particular, the cell culture medium may have an albumin concentration of at least 0.3 millimolar (mM). It has been found that a 2× increase in albumin concentration significantly improved clonal survival of hES cells on a laminin-521/E-Cadherin matrix. Table 5 below provides a formulation for a cell culture medium containing additional albumin.

In particular embodiments, the amount of human serum albumin (HSA) can be varied from a concentration of 0.195 mM to 1 mM, including from 0.3 mM to 1 mM or from 0.3 mM to about 0.4 mM. The amount of bFGF can also be varied from 0 to about 105 ng/mL, or from 0 to 3.9 ng/mL, or from 0.5 ng/mL to 3.5 ng/mL. These two variations in the amount of HSA and bFGF may occur independently or together.

TABLE 5 mTeSR1 formulation.

| mTeSR1 Ingredient | molar mass (g/mol) | Concentration (ng/mL) | Concentration (mM) |
|---|---|---|---|
| INORGANIC SALTS | | | |
| Calcium chloride (Anhydrous) | 110.98 | 9.14E+04 | 8.24E−01 |
| HEPES | 238.3 | 2.81E+06 | 1.18E+01 |
| Lithium Chloride (LiCl) | 42.39 | 4.15E+04 | 9.80E−01 |
| Magnesium chloride (Anhydrous) | 95.21 | 2.26E+04 | 2.37E−01 |
| Magnesium Sulfate ($MgSO_4$) | 120.37 | 3.84E+04 | 3.19E−01 |
| Potassium chloride (KCl) | 74.55 | 2.43E+05 | 3.26E+00 |
| Sodium bicarbonate ($NaHCO_3$) | 84.01 | 1.51E+06 | 1.80E+01 |
| Sodium chloride (NaCl) | 58.44 | 5.53E+06 | 9.46E+01 |
| Sodium phosphate, dibasic (Anhydrous) | 141.96 | 5.56E+04 | 3.92E−01 |
| Sodium phosphate, monobasic monohydrate ($NaH_2PO_4$—$H_2O$) | 137.99 | 4.90E+04 | 3.55E−01 |
| TRACE MINERALS | | | |
| Ferric Nitrate ($Fe(NO_3)_3$—$9H_2O$) | 404 | 3.92E+01 | 9.71E−05 |
| Ferrous sulfate heptahydrate ($FeSO_4$—$7H_2O$) | 278.01 | 3.28E+02 | 1.18E−03 |
| Copper(II) sulfate pentahydrate ($CuSO_4$—$5H_2O$) | 249.69 | 1.02E+00 | 4.08E−06 |
| Zinc sulfate heptahydrate ($ZnSO_4$—$7H_2O$) | 287.56 | 3.39E+02 | 1.18E−03 |
| Ammonium Metavanadate $NH_4VO_3$ | 116.98 | 1.28E+00 | 1.09E−05 |
| Manganese Sulfate monohydrate ($MnSO_4$—$H_2O$) | 169.02 | 3.33E−01 | 1.97E−06 |
| $NiSO_4$—$6H_2O$ | 262.85 | 2.55E−01 | 9.70E−07 |
| Selenium | 78.96 | 1.40E+01 | 1.77E−04 |
| Sodium Meta Silicate $Na_2SiO_3$ $9H_2O$ | 284.2 | 2.75E+02 | 9.66E−04 |
| $SnCl_2$ | 189.62 | 2.35E−01 | 1.24E−06 |
| Molybdic Acid, Ammonium salt | 1235.86 | 2.43E+00 | 1.97E−06 |
| $CdCl_2$ | 183.32 | 2.24E+00 | 1.22E−05 |
| $CrCl_3$ | 158.36 | 3.14E−01 | 1.98E−06 |
| $AgNO_3$ | 169.87 | 1.67E−01 | 9.81E−07 |
| $AlCl_3$ $6H_2O$ | 241.43 | 1.18E+00 | 4.87E−06 |
| Barium Acetate ($Ba(C_2H_3O_2)_2$) | 255.42 | 2.50E+00 | 9.79E−06 |
| $CoCl_2$ $6H_2O$ | 237.93 | 2.33E+00 | 9.81E−06 |
| $GeO_2$ | 104.64 | 5.20E−01 | 4.97E−06 |
| KBr | 119 | 1.18E−01 | 9.89E−07 |
| KI | 166 | 1.66E−01 | 1.00E−06 |

TABLE 5-continued mTeSR1 formulation.

| mTeSR1 Ingredient | molar mass (g/mol) | Concentration (ng/mL) | Concentration (mM) |
|---|---|---|---|
| NaF | 41.99 | 4.13E+00 | 9.83E−05 |
| RbCl | 120.92 | 1.19E+00 | 9.81E−06 |
| ZrOCl$_2$ 8H$_2$O | 178.13 | 1.75E+00 | 9.80E−06 |
| ENERGY SUBSTRATES | | | |
| D-Glucose | 180.16 | 2.47E+06 | 1.37E+01 |
| Sodium Pyruvate | 110.04 | 4.31E+04 | 3.92E−01 |
| LIPIDS | | | |
| Linoleic Acid | 280.45 | 5.27E+01 | 1.88E−04 |
| Lipoic Acid | 206.33 | 8.25E+01 | 4.00E−04 |
| Arachidonic Acid | 304.47 | 3.93E+00 | 1.29E−05 |
| Cholesterol | 386.65 | 4.33E+02 | 1.12E−03 |
| DL-alpha tocopherol-acetate | 472.74 | 1.37E+02 | 2.90E−04 |
| Linolenic Acid | 278.43 | 1.95E+01 | 6.99E−05 |
| Myristic Acid | 228.37 | 1.96E+01 | 8.59E−05 |
| Oleic Acid | 282.46 | 1.96E+01 | 6.94E−05 |
| Palmitic Acid | 256.42 | 1.96E+01 | 7.65E−05 |
| Palmitoleic acid | 254.408 | 1.96E+01 | 7.71E−05 |
| Stearic Acid | 284.48 | 1.96E+01 | 6.89E−05 |
| AMINO ACIDS | | | |
| L-Alanine | 89.09 | 1.22E+04 | 1.37E−01 |
| L-Arginine hydrochloride | 147.2 | 8.07E+04 | 5.48E−01 |
| L-Asparagine-H$_2$O | 150.13 | 2.06E+04 | 1.37E−01 |
| L-Aspartic acid | 133.1 | 1.82E+04 | 1.37E−01 |
| L-Cysteine-HCl-H$_2$O | 175.63 | 1.38E+04 | 7.83E−02 |
| L-Cystine dihydrochloride | 313.22 | 2.45E+04 | 7.83E−02 |
| L-Glutamic acid | 147.13 | 2.02E+04 | 1.37E−01 |
| L-Glutamine | 146.15 | 4.30E+05 | 2.94E+00 |
| Glycine | 75.07 | 2.21E+04 | 2.94E−01 |
| L-Histidine monohydrochloride monohydrate | 209.63 | 2.47E+04 | 1.18E−01 |
| L-Isoleucine | 131.17 | 4.28E+04 | 3.26E−01 |
| L-Leucine | 131.17 | 4.64E+04 | 3.54E−01 |
| L-Lysine hydrochloride | 182.65 | 7.14E+04 | 3.91E−01 |
| L-Methionine | 149.21 | 1.35E+04 | 9.06E−02 |
| L-Phenylalanine | 165.19 | 2.79E+04 | 1.69E−01 |
| L-Proline | 115.13 | 2.49E+04 | 2.16E−01 |
| L-Serine | 105.09 | 3.09E+04 | 2.94E−01 |
| L-Threonine | 119.12 | 4.19E+04 | 3.52E−01 |
| L-Tryptophan | 204.23 | 7.07E+03 | 3.46E−02 |
| L-Tyrosine disodium salt hydrate | 225.15 | 3.78E+04 | 1.68E−01 |
| L-Valine | 117.15 | 4.16E+04 | 3.55E−01 |
| VITAMINS | | | |
| Ascorbic acid | 176.12 | 4.46E+04 | 2.53E−01 |
| Biotin | 244.31 | 2.74E+00 | 1.12E−05 |
| B12 | 1355.37 | 5.34E+02 | 3.94E−04 |
| Choline chloride | 139.62 | 7.02E+03 | 5.03E−02 |
| D-Calcium pantothenate | 238.27 | 8.79E+02 | 3.69E−03 |
| Folic acid | 441.4 | 2.08E+03 | 4.71E−03 |
| i-Inositol | 180.16 | 9.89E+03 | 5.49E−02 |
| Niacinamide | 122.12 | 1.59E+03 | 1.30E−02 |
| Pyridoxine hydrochloride | 205.64 | 1.57E+03 | 7.62E−03 |
| Riboflavin | 376.36 | 1.72E+02 | 4.56E−04 |
| Thiamine hydrochloride | 337.27 | 8.16E+03 | 2.42E−02 |
| GROWTH FACTORS/PROTEINS | | | |
| GABA | 103.12 | 1.01E+05 | 9.79E−01 |
| Pipecolic Acid | 129 | 1.27E+02 | 9.84E−04 |
| bFGF | 18000 | 1.04E+02 | 5.77E−06 |
| TGF beta 1 | 25000 | 5.88E−01 | 2.35E−08 |
| Human Insulin | 5808 | 2.28E+04 | 3.92E−03 |
| Human Holo-Transferrin | 78500 | 1.08E+04 | 1.37E−04 |
| Human Serum Albumin | 67000 | 1.31E+07 | 1.95E−01 |
| Glutathione (reduced) | 307.32 | 1.96E+03 | 6.38E−03 |
| OTHER COMPONENTS | | | |
| Hypoxanthine Na | 136.11 | 1.61E+03 | 1.18E−02 |
| Phenol red | 354.38 | 5.99E+03 | 1.69E−02 |
| Putrescine-2HCl | 161.07 | 6.36E+03 | 3.95E−04 |
| Thymidine | 242.229 | 2.86E+02 | 1.18E−03 |
| 2-mercaptoethanol | 78.13 | 7.66E+03 | 9.80E−02 |
| Pluronic F-68 | 8400 | 1.96E+05 | 2.33E−02 |
| Tween 80 | 1310 | 4.31E+02 | 3.29E−04 |

The systems containing a LN-521/e-cadherin substrate and mTeSR1 medium with additional albumin work extremely well for maintaining and proliferating undifferentiated stem cells (e.g. embryonic and induced pluripotent stem cells) in a completely chemically defined environment and xeno-free conditions without feeders or any inhibitors of apoptosis.

The combination of the laminin substrate with the cell culture medium of the present disclosure results in a cell culture system that can be cheaper, yet provides higher efficiency in maintaining pluripotent stem cells. In essence, all that is required is a laminin and a minimal amount of nutrition. It is particularly contemplated that the laminin used in combination with this cell culture medium is either LN-511 or LN-521.

The cell culture substrate and the cell culture medium do not contain any differentiation inhibitors, feeder cells, differentiation inductors, or apoptosis inhibitors.

The single stem cell removed from the embryo can proliferate into one or more descendant pluripotent stem cells. Once a sufficient number of such descendant stem cells exist, they can be replated onto a new cell culture substrate that includes the laminin but does not have the cadherin. The cadherin is no longer needed, as the stem cells can signal to each other instead.

The cell culture substrate and cell culture medium are completely xeno-free, which is very helpful and useful. Another advantage of this procedure is that the descendant stem cells are homogeneous pluripotent cells, rather than clusters that contain partially differentiated and possibly tumorigenic cells. In addition, they are useful for the HLA typed stem cell bank because in vitro cell lines tend to acquire growth-promoting mutations, and these faster growing cells form a large proportion of the cell line from passage to passage. This change is not optimal for cell populations that will be used for transplantation. The substrate and medium of the present disclosure can avoid high numbers of passages, reducing this risk.

After the single stem cell is successfully expanded, the stem cells may be stored to form the stem cell bank. Typically, the stem cells are frozen, using liquid nitrogen or other methods known in the art.

Alternatively, the single stem cell is subjected to HLA serotyping before being stored to form the stem cell bank. Otherwise, after the single stem cell is successfully expanded and stable, e.g. having been expanded for five to ten passages on various types of laminin or e-cadherin matrices, the single stem cell could be subjected to HLA serotyping.

Tissue typing may occur at a tissue typing facility. Preliminary tissue typing can also be performed by a tissue typing assay. The tissue typing assay may be performed on the blood sample taken from a stem cell donor. White blood cells are isolated from the donor blood sample, i.e. through centrifugation, and are further used in either serological or DNA testing. Entire white blood cells are required for serological testing, while only the DNA extracted from white blood cells is required for DNA testing. Further high resolution HLA serotyping can be performed at an industrial scale facility, such as those which implement sequence-specific oligonucleotide primed PCR (PCR-SSO) based typing techniques.

Preliminary tissue typing performed through either serological or DNA methods may be performed by a haplotype analyzer. The haplotype analyzer may be any tool recognized by one skilled in the art to determine the genetic haplotype of a white blood cell or DNA sample.

The single stem cell may also be further subjected to microbial testing after tissue typing for diseases, e.g. mycoplasma, HIV, hepatitis B, C, HTLV1 and 2, syphilis, CMV), despite negative tests from donors.

An exemplary HLA serotype stem cell bank may include at least 50 cryotubes with at least one million stem cells of each HLA serotype stem cell line. A clinical grade cryopreservation medium should be utilized for slow programmed freezing of cell lines. An exemplary cryopreservation medium is Stem-Cellbanker®, produced by Zenoaq in Japan. This is a chemically defined freezing medium which is completely free of serum and animal derived components, and contains only USP, EP or JP graded ingredients. The cryotubes are closed, sealed, and placed in a larger sealed tube which is part of a safety system. The tubes are stored within liquid nitrogen to guarantee the low temperature required by some descendant stem cells. The stem bank includes an infrastructure with automated liquid nitrogen filling and temperature control systems.

A kit for performing the methods described herein will include a cell culture substrate, a cell culture medium, a cell splitting solution, a haplotype analyzer, and a freezing medium as described above.

The present disclosure has been described with reference to exemplary embodiments. Obviously, modifications and alterations will occur to others upon reading and understanding the preceding detailed description. It is intended that the present disclosure be construed as including all such modifications and alterations insofar that they come within the scope of the appended claims or the equivalents thereof.

The invention claimed is:

1. A method for forming a stem cell bank, comprising:
   obtaining a first stem cell from a multi-cell fertilized embryo;
   expanding the first stem cell into two or more descendant stem cells; and
   storing at least one of the descendant stem cells to form the stem cell bank,
   wherein the first stem cell is expanded by placing the first stem cell on a cell culture substrate comprising a laminin and a cadherin, wherein the laminin is an intact protein or a protein fragment;
   wherein the laminin is laminin-521 or laminin-511;
   and wherein the weight ratio of the laminin to the cadherin is from about 5:1 to about 15:1.

2. The method of claim 1, wherein the cadherin is e-cadherin.

3. The method of claim 1, wherein the cell culture substrate does not contain any differentiation inhibitors, feeder cells, differentiation inductors, or apoptosis inhibitors.

4. The method of claim 1, further including applying a cell culture medium to the first stem cell.

5. The method of claim 4, wherein the cell culture medium has an albumin concentration of at least 0.3 mM.

6. The method of claim 1, further comprising replating the descendant stem cells on a new cell culture substrate comprising a laminin, wherein the laminin is an intact protein or a protein fragment.

7. The method of claim 1, wherein the multi-cell fertilized embryo has from 8 to 32 total cells.

8. The method of claim 1, further comprising determining the human leukocyte antigen (HLA) serotype of the first stem cell or the two or more descendant stem cells.

9. The method of claim 8, wherein determining the HLA serotype includes determining whether the two or more descendant stem cells are homozygous at a given HLA locus.

10. The method of claim 9, wherein the given HLA locus is the HLA-A, HLA-B, or DR locus.

11. The method of claim 8, wherein the HLA serotype is determined by PCR-SSO.

12. A kit for creating a stem cell bank, comprising:
   a cell culture substrate comprising a laminin and a cadherin, wherein the laminin is an intact protein or a protein fragment, wherein the laminin is laminin-521 or laminin-511, and wherein the weight ratio of the laminin to the cadherin is from about 5:1 to about 15:1;
   a cell culture medium;
   a cell splitting solution;
   a freezing medium; and
   a HLA serotype analyzer.

13. The kit of claim 12, wherein the cadherin is e-cadherin.

14. The kit of claim 12, wherein the cell culture substrate consists of the laminin and the cadherin.

15. The kit of claim 12, wherein the cell culture substrate does not contain any differentiation inhibitors, feeder cells, differentiation inductors, or apoptosis inhibitors.

* * * * *